United States Patent [19]

Shrum

[11] 4,081,983

[45] Apr. 4, 1978

[54] MOLDS FOR THE CONTINUOUS CASTING OF METALS

[76] Inventor: Lorne Russell Shrum, 820 Manchester Road, London, Ontario, Canada, N6H 4J6

[21] Appl. No.: 782,364

[22] Filed: Mar. 29, 1977

[51] Int. Cl.² .................................................. B21D 26/08
[52] U.S. Cl. ........................................ 72/56; 29/421 E
[58] Field of Search ..................... 72/54, 56; 29/421 E

[56] References Cited

U.S. PATENT DOCUMENTS

| | | | |
|---|---|---|---|
| 2,969,758 | 1/1961 | Howlett, Jr. et al. | 29/421 E X |
| 3,153,848 | 10/1964 | Slyman et al. | 29/421 E |
| 3,160,952 | 12/1964 | Carney et al. | 29/421 E X |
| 3,172,199 | 3/1965 | Schmidt | 29/421 E |
| 3,364,561 | 1/1968 | Barrington | 29/421 E X |
| 3,433,039 | 3/1969 | Henninsen | 72/56 |
| 3,927,546 | 12/1975 | Shrum | 72/56 |

Primary Examiner—Leon Gilden

[57] ABSTRACT

In order to reduce stresses applied to mold sleeves and arbors during explosive forming of tubular copper molds for continuous casting of metals, forming is carried out by applying and detonating in turn successive groups of peripherally spaced explosive charges extending longitudinally of the exterior of the mold, the charges being placed so that at least one charge is detonated adjacent each portion of the external surface of the mold.

10 Claims, 3 Drawing Figures

MOLDS FOR THE CONTINUOUS CASTING OF METALS

FIELD OF THE INVENTION

The present invention relates to a method of forming a tubular copper mold for the continuous casting of metals, particularly steel.

BACKGROUND OF THE INVENTION

In my U.S. Pat. No. 3,927,546, issued Oct. 15, 1974, I describe a method for the explosive forming or reforming of tubular copper molds for the continuous casting of metals, which has proved highly successful with the smaller sizes of mold. In the case of the larger sizes of mold certain problems can arise. Large molds often have substantial wall thicknesses, in a typical example approximately 4 cm. in a rectangular mold having internal cross-sectional dimensions of 25 cm. × 30 cm. An important advantage of the invention is that the forming process is combined with a highly advantageous hardening of the copper on the inside of the mold, but it is found that, with large molds with thick walls, the size of the explosive charge required to produce the required forming effect, and more particularly the required degree of hardening, may be such as to damage the mold and possibly the arbor on which mold is formed. In order for the required effect to be achieved, the magnitude of the shock applied by the explosive to the copper must be such as to cause it plastically to deform against the arbor so as to cause it to assume the profile of the mold and to receive the necessary work hardening. With large wall thicknesses, the necessary magnitude of shock tends only to occur in those areas where the external surface of the mold is covered by the explosive charge: this means that the charge in effect must completely jacket the mold. This not only implies a rather substantial charge, but also means that it is difficult to control the detonation pattern of the explosive so as to produce the required solely longitudinal end-to-end detonation of the charge. The large charge results in heavy stresses being applied to the arbor, whilst an incorrect detonation pattern can lead to damage to the mold itself, or failure of the mold to assume the required configuration with sufficient accuracy since the arbor becomes strained out of shape either elastically and therefore momentarily during the forming process, or permanently. Moreover, since the arbors are expensive to produce, it is undesirable that they be subject to stresses that might substantially shorten their lives. I have found that in order to obtain accurately formed molds it is important to use the smallest explosive charges that will reliably provide the required forming and hardening effect, and it is also important that detonation occurs solely longitudinally of the mold, as specified in my patent, if twisting and other deformations of the mold are not to occur.

A further problem arises in the forming of molds of large dimensions. Such molds are most conveniently and economically formed from cast sleeves. Before forming a sleeve, it is necessary to grind its inner surface to remove residual casting sand, scale and oxide and localized casting defects. This grinding may leave substantial depressions as much as 5 millimeters deep in the inner surface of the sleeve which can be difficult to remove during the forming operation and still further increase the size of the explosive charge which must be used.

Finally, with large molds there are severe practical problems in providing facilities for containing the explosion of the quite large quantities of explosives needed to provide the required forming forces.

OBJECT OF THE INVENTION

The object of the invention is to provide an explosive forming technique for continuous casting molds which may be applied even to very large, thick-walled molds without excessively stressing the mold sleeve and without requiring elaborate facilities for containing the explosions involved.

SUMMARY OF THE INVENTION

I have now found that this object can be achieved by applying and detonating the total explosive charge in a plurality of successive groups of charges in which the charges in each group are peripherally spaced from one another and extend longitudinally essentially parallel to the longitudinal axis of the mold, but when taken together cover more or less the entire outer surface of the sleeve or mold to be formed. The method used is thus basically that claimed in my U.S. Pat. No. 3,927,546, but with the improvement that a plurality of longitudinally extending charges are applied adjacent the sleeve in a plurality of successive groups each of at least one charge, charges in the same group being spaced from one another about the periphery of the sleeve and each group of charges being detonated prior to the application of charges of a succeeding group, the charges in successive groups being distributed so that at least one charge is detonated adjacent every portion of the external surface of the sleeve. By this means, stresses tending to damage the sleeve or arbor are greatly reduced, and by examining the sleeve after the detonation of each group of charges, subsequent groups can be adjusted or supplemented, or additional groups added so as to ensure satisfactory forming. Supplementary local charges may be added to the first and/or subsequent groups in order to eliminate local depressions on the inner surface of the mold.

Further features of the invention will become apparent from the following description of embodiments of the invention.

SHORT DESCRIPTION OF THE DRAWINGS

In the drawings:

FIG. 1 is a perspective view, partially cut away, of an arbor and sleeve assembly with a group of explosive charges applied thereto, FIG. 2 is a diagrammatic end view of a mold sleeve, and FIG. 3 is a diagrammatic side elevation of the same sleeve.

DESCRIPTION OF THE PREFERRED EMBODIMENTS

Figure 1:
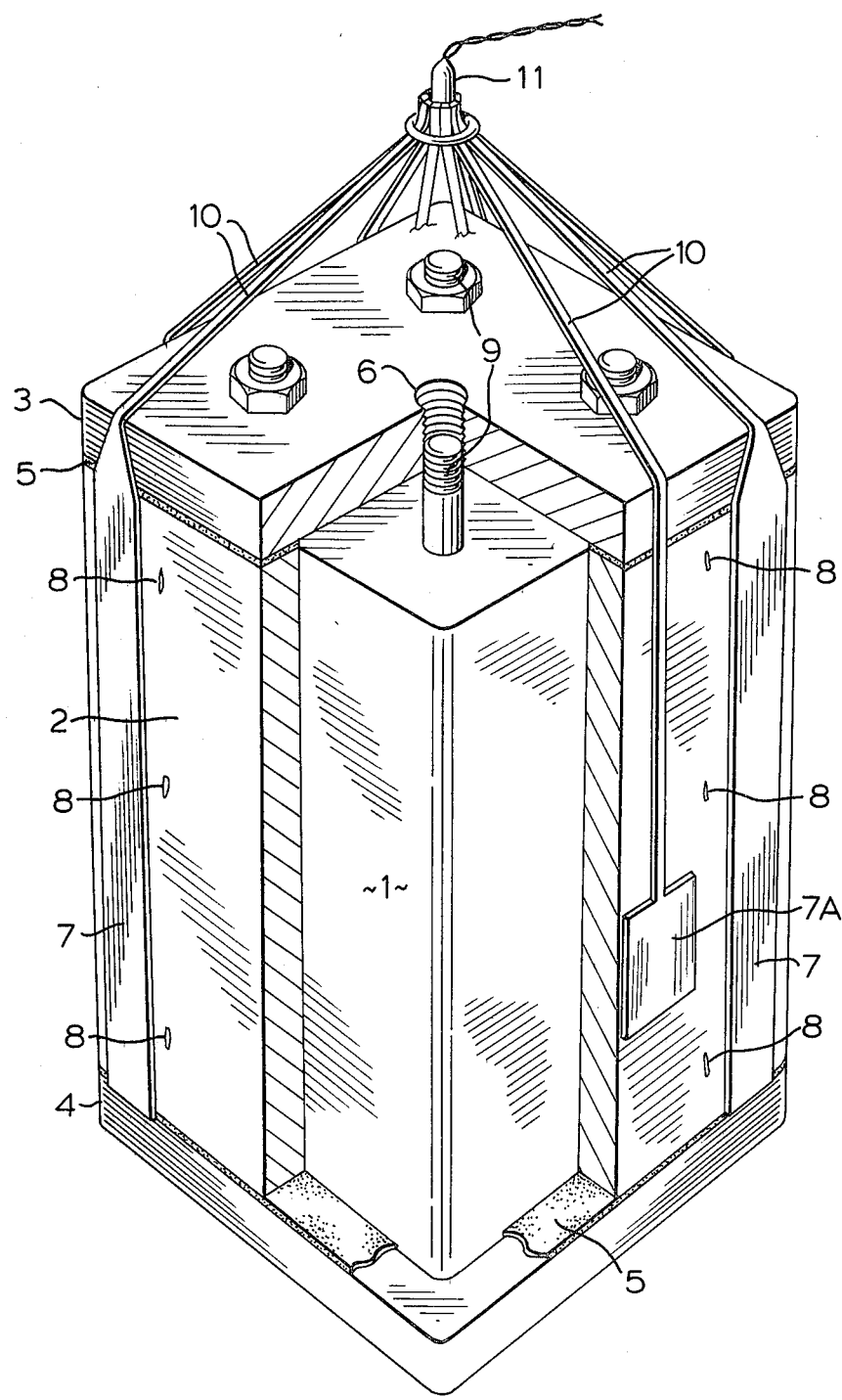

The procedures employed in the exercise of the present invention are in many respects similar to those described in my U.S. Pat. No. 3,927,546, the text of which is herein incorporated by reference, and thus only the differences will be described in detail. The references used in FIG. 1 of the present application are the same as those in the Figure of U.S. Pat. No. 3,927,546, with some additions.

Assuming that a mold is to be formed from a cast copper sleeve, the sleeve is prepared by grinding its internal surface to remove sand, oxide and localized defects, and its ends are machined flat so as to be able to maintain an airtight seal with an end plate, with the assistance of an interposed gasket. The internal surface of the sleeve 2 thus produced is examined, and the external surface marked opposite the location of any substantial depressions remaining after the grinding steps.

The external surface is also marked out to indicate the location of the explosive charges to be applied thereto. In order to ensure survival of the markings during the forming process, these may be a series of chisel cuts 8 spaced along the centre lines of the locations to which charges are to be applied. They will be largely obliterated by explosion of the charges applied thereover, thus indicating which areas have been formed. The layout of the groups of charges is discussed further below.

The prepared sleeve is placed over an arbor, whose external surface has the configuration and finish required of the finished mold. End plates 3 and 4, are placed in position over the ends of the sleeve with the interposition of gaskets 5. The assembly is secured together by through bolts 9 and any air between the arbor 1 and the sleeve 2 is evacuated through an exhaust passage 6 to avoid the presence of air pockets which might interfere with the forming process. A first group of explosive charges 7, 7a is then applied to the external surface of the sleeve 2, the upper ends of the charges being connected by equal lengths of explosive cord 10 to a detonator 11, the entire assembly is fully submerged in a pit filled with water, and the charges detonated by means of the detonator 11 and the cord 10.

The assembly is then removed from the pit and disassembled, the internal surface of the sleeve is examined, the external surface is marked up to indicate any changes required as a result of the examination in subsequent groups of explosive charges to be applied to the sleeve, and the entire process is repeated as many times as there are groups of charges to be applied. Since the forming operation causes a slight increase in the length of the sleeve, this is machined to the exact length required as a final step in the process. This increase in length is greatest adjacent the outer surface of the sleeve, somewhat less adjacent the inner surface, and least intermediate the inner and outer surfaces.

The layout of the explosive charges in the various groups is best discussed with reference to a specific example of the production of a rectangular mold for casting steel blooms, the mold having internal cross-sectional dimensions of 26.67 cm. × 31.75 cm., a nominal length of 71.1 cm., and a wall thickness of about 4 cm. A sleeve is cast to these nominal dimensions from electrolytic copper, which may contain 0.08% silver, and has a yield strength as cast of approximately 9000 p.s.i. The internal surfaces of the sleeve are ground, and its ends machined as previously described to give an actual overall length of 71.1 cm. and provide end surfaces on the sleeve which are capable of entering sealing engagement with the gaskets 5. With such a mold, it is found that in order to achieve adequate hardening of the inner surfaces of the sleeve, it is necessary to detonate explosive adjacent substantially the entire outer surface of the sleeve; a charge equivalent to covering the entire outside surfaces with the sheet explosive Detasheet (Registered Trade Mark) C manufactured by DuPont having a weight of 1 gm. per square inch will usually provide sufficient forming and hardening except in areas where the preparatory grinding of the sleeve has formed deep depressions in the inside surfaces. Such a charge amounts to no less than 1.6 kilograms and because of its size would present a substantial problem in containment quite apart from the risk of damaging the sleeve or the arbor. Moreover, with such a continuous sheet of explosive it is essential that detonation is initiated and proceeds simultaneously around the entire periphery of the mold since otherwise the detonation front will not proceed purely longitudinally from end to end of the sleeve and unbalanced forces will be applied tending to bend or twist both the mold or the arbor. Although such simultaneous initiation of detonation is perfectly feasible, it requires considerable skill and perfect materials to assure it, and any error or misfire is likely to ruin an expensive sleeve and/or arbor.

I have found that substantially the same total forming and hardening effect can be obtained when the explosive is divided into a number of much smaller charges applied and detonated in successive stages, whilst the disadvantages resulting from the use of a single large charge are overcome. The number of stages should not be unnecessarily multiplied because of the labor involved in disassembling and reassembling the sleeve/arbor assembly between each stage. In the example being discussed I have found that by applying and detonating the explosive in three stages each comprised of a number of small charges, the individual explosions are reduced to manageable proportions and should an individual charge misfire, the remaining charges will still detonate longitudinally, and the out of balance forces involved are small enough to make it unlikely that any serious damage will occur to the sleeve or the arbor.

In earlier tests the charges were applied in five successive groups, which gave equally satisfactory results although involving more labor, and if adequate facilities for containing the explosions were available, a reduction to two groups would probably be possible although not necessarily advantageous since the capability of making corrective adjustments in the charges applied in successive groups during the course of the forming operation is obviously reduced. Should examination after detonation of the planned stages show insufficient forming or hardening to have been achieved, additional stages may be added until the desired results are achieved. Generally speaking, the number of stages desirable will increase with the size of the mold, its wall thickness and the extent of the defects in its internal surface. Localized defects or depressions in the internal walls of the sleeve may be corrected by supplementary charges applied either together with those comprised in the main forming stages, or in separate preliminary, intermediate or subsequent stages comprising one or more small supplementary charges.

Figure 2:
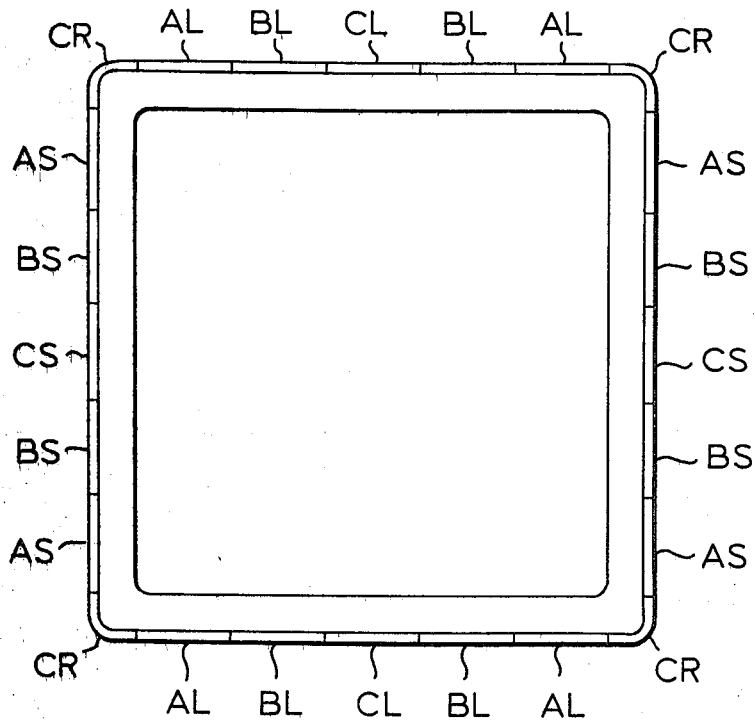
Figure 3:
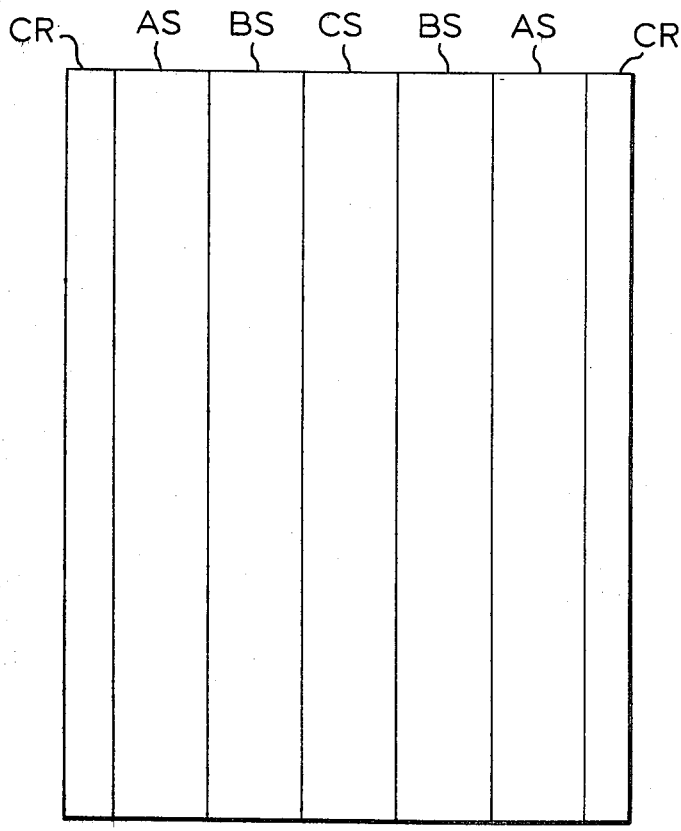

Although in the example being considered, adequate hardening of the copper adjacent the inner surfaces of the sleeve is only achieved where explosive is detonated against the opposite portion of the outer surface, there will be some hardening of the remaining copper, with the result that successive groups of charges will have progressively less effect. It is therefore desirable that the charges forming the first or earlier stages be applied to those portions of the sleeve requiring the most working, i.e. adjacent the corners and over the larger defects or depressions in the inside walls of the sleeve. In the example, and referring to FIGS. 2 and 3, the first stage comprises eight charges formed by strips AS and AL of 1 gram/sq. in. Detasheet sheet explosive applied as shown in the Figures using an adhesive. The strips AS applied to the short outside faces of the sleeve opposite the longitudinal edge portions of the inner surfaces are 5.7 cm. wide, and the strips AL applied to the corresponding portions of the long outside faces are 6.35 cm. wide, all of the strips being 71 cm. long. In addition to these eight charges, patches of the same explosive sheet are applied over the depressions whose locations have been indicated on the outside surfaces of the sleeve, the size of the patches being in accordance with the degree of correction required. After detonation of the charges of the first stage, the interior of the sleeve is examined to ensure that a satisfactory degree of forming has been achieved, and any remaining internal defects which it is estimated will not be corrected during the detonation of subsequent stages without modification of the charges are noted on the outside surface so that supplementary charges may be added in appropriate areas.

The second stage comprises eight charges formed by strips BS and BL of Detasheet sheet explosive of the same respective dimensions as the strips AS and AL, but applied to areas of the short and long outside surfaces of the sleeve inwardly of and abutting the areas to which the strips AS and AL were applied. The stage also includes any supplementary charges judged necessary after as a result of the examination which followed the first stage.

The third stage also comprises eight charges formed by strips CR, CS and CL. The strips CR are 5.7 cm. wide and are applied to the corners of the sleeve so as to cover the areas between those covered by the strips AS and AL, and the strips CS and CL are respectively 5.7 cm. and 6.9 cm. wide and are applied to the areas of the short and long outside surface between the strips BS and between the strips BL. The third stage also includes any charges required to correct defects in the inner surfaces noted during examination of the sleeve after the second stage and not expected to be corrected by the charges CR, CS and CL.

If any portions of the interior surface remain insufficiently formed after the third stage, suitably disposed fourth and subsequent stages may be utilized until the desired result is achieved.

The total weight of the eight basic charges used in each of the three stages is 532 grams. In an actual example these totals were increased to 550 grams, 590 grams and 570 grams by the additional explosive used for correcting local defects, but these additions will obviously vary from mold to mold.

Although the use of sheet explosive has been described, and such explosive is the most convenient to apply, other forms of explosive such as cord explosive (for example, that sold by DuPont under the trademark Primacord) could be utilized if applied in such a manner as to obtain the desired coverage, explosive force, and longitudinal detonation paths. Thus strips of sheet explosive could be replaced by groups of parallel explosive cords, or by closely spaced narrow parallel strips of thicker or more powerful sheet explosive, provided that the total effect of the detonation of the charges in the various stages is that explosive is detonated adjacent portions of the outside surfaces of the sleeve substantially opposite every portion of the inside surfaces of the sleeve, the width of any portion of the external periphery of the sleeve not directly subjected to explosive action being small compared with the wall thickness of the sleeve. The explosive used should meet the requirements set out in my U.S. Pat. No. 3,927,546. Stand-offs may be used as described in that patent, although this will not normally be necessary or desirable if suitable explosive material is used. Great care should be taken to avoid trapping air between the explosive and the sleeve, since this can result in severe local external damage to the sleeve.

After forming, the ends of the sleeve are again machined so as once more to reduce its length to 81.1 centimeters, thus compensating for the increase of length that takes place during forming.

The process of the invention is equally applicable to the reforming of used molds. In this case however the preliminary grinding and machining will usually be unnecessary if the molds are merely worn as opposed to damaged and repaired. Areas of heavy wear may be noted for the application of supplementary charges as before, and the charges are calculated or estimated bearing in mind that the metal of the mold will already be at least partially hardened (unless the mold has been annealed prior to reforming).

What I claim is:

1. In a method of forming tubular copper molds for the continuous casting of metals, in which an arbor is formed having an external surface having the profile and finish required of the finished mold, a copper sleeve of the same general shape as the mold is fitted on the arbor, charges of high explosive material extending longitudinally substantially parallel to the longitudinal axis of the mold are applied to the exterior of the sleeve so as to provide detonation paths extending from one end of the sleeve to the other, air is evacuated from between the sleeve and the arbor, the sleeve with the charges applied thereto is fully immersed in a liquid, and the charges are detonated from one end of the sleeve so as to apply a longitudinally travelling shock wave of sufficient magnitude to cause plastic flow of the material of the sleeve into intimate contact with the arbor, the improvement in which the plurality of longitudinally extending charges are applied adjacent the sleeve in a plurality of successive groups each of at least one charge, charges in the same group being spaced from one another about the periphery of the sleeve and each group of charges being detonated prior to the application of charges of a succeeding group, the charges in successive groups being distributed so that at least one charge is detonated adjacent every portion of the external surface of the sleeve.

2. A method according to claim 1, wherein the charges include supplementary charges applied adjacent the external surface of the sleeve over locations where local depressions have been noted on the internal surface of the sleeve.

3. A method according to claim 2, wherein the supplementary charges are included in the first group of charges to be applied.

4. A method according to claim 3, wherein further supplementary charges in the same locations are included in a subsequent group of charges should the depressions persist.

5. A method according to claim 1, wherein the sleeve is withdrawn from the arbor for examination after the detonation of each group of charges, and supplementary charges are included in subsequent groups to correct local deficiencies in the progress of the forming operation.

6. A method according to claim 1, wherein the sleeve is rectangular, and the charges of the first group to be applied comprise charges adjacent those portions of the external surface of the sleeve opposite those portions of the internal surface of the sleeve adjacent its corners.

7. A method according to claim 6, wherein three groups of charges are applied, the first group comprising eight charges applied to portions of the external faces of the rectangular sleeve opposite the longitudinal edge portions of the internal faces of the sleeve, the second group comprising eight charges applied to portions of the external faces of the sleeve abutting and inward of the areas to which the charges of the first group were applied, and the third group comprising eight charges applied to the external corners and to the center portions of the external faces of the sleeve, the charges each being of such a width that substantially the entire outer surface of the sleeve has a charge detonated adjacent thereto, and the total quantity of explosive applied in each group is approximately equal.

8. A method according to claim 7, wherein at least the first group of charges includes supplementary charges applied to the external surface of the sleeve opposite known depressions in the internal surface of the sleeve.

9. A method according to claim 1, wherein the total quantity of explosive utilized is divided approximately equally between the different groups of charges.

10. A method according to claim 9, wherein the charges in each group are symmetrically arranged around the periphery of the sleeve, and each charge is applied to a different portion of the outer periphery of the sleeve.

* * * * *